United States Patent
Pedrazzini

(10) Patent No.: US 8,465,693 B2
(45) Date of Patent: Jun. 18, 2013

(54) APPARATUS FOR AUTOMATICALLY DEPOSITING, PRESERVING AND RETRIEVING BIOLOGICAL MATERIAL SPECIMENS IN A REFRIGERATED STORAGE

(75) Inventor: Gianandrea Pedrazzini, Paradiso (CH)

(73) Assignee: Inpeco Holding Ltd., Valletta (MT)

( * ) Notice: Subject to any disclaimer, the term of this patent is extended or adjusted under 35 U.S.C. 154(b) by 337 days.

(21) Appl. No.: 12/809,393

(22) PCT Filed: Dec. 12, 2008

(86) PCT No.: PCT/EP2008/067459
§ 371 (c)(1),
(2), (4) Date: Jun. 18, 2010

(87) PCT Pub. No.: WO2009/077465
PCT Pub. Date: Jun. 25, 2009

(65) Prior Publication Data
US 2010/0303590 A1 Dec. 2, 2010

(30) Foreign Application Priority Data
Dec. 19, 2007 (IT) .............................. MI2007A2386

(51) Int. Cl.
*G01N 35/04* (2006.01)
(52) U.S. Cl.
USPC ............... 422/65; 422/63; 414/277; 414/279; 414/281; 414/284; 414/286
(58) Field of Classification Search
USPC .............. 422/63, 65, 300; 414/279, 277, 284, 414/281, 286
See application file for complete search history.

(56) References Cited

U.S. PATENT DOCUMENTS

| | | | |
|---|---|---|---|
| 3,679,040 A | 7/1972 | Kretzschmar et al. | |
| 6,068,437 A | 5/2000 | Boje et al. | |
| 6,190,117 B1 * | 2/2001 | Lichti | ............................ 414/800 |
| 6,685,884 B2 * | 2/2004 | Stylli et al. | ........................ 422/63 |
| 7,214,023 B2 | 5/2007 | Sato et al. | |
| 2004/0037680 A1* | 2/2004 | Sato et al. | ....................... 414/281 |
| 2007/0172396 A1 | 7/2007 | Neeper et al. | |
| 2010/0028124 A1* | 2/2010 | Lackner et al. | ................ 414/806 |

FOREIGN PATENT DOCUMENTS
EP 1 757 882 A2 2/2007

* cited by examiner

*Primary Examiner* — P. Kathryn Wright
(74) *Attorney, Agent, or Firm* — Birch, Stewart, Kolasch & Birch, LLP

(57) ABSTRACT

An apparatus for automatically depositing, preserving and retrieving biological material test tubes is described, including a refrigerated storage with movable horizontal shelves and a conveyor interface, adapted to automatically transport biological material test tubes, a device adapted to handle the test tubes between the interface and the containers of a sorted plurality of test tubes, the containers having toothed guides and being able to be placed on the lanes of a bench, a handling device of the containers between the bench and an access area of the storage, slidingly mounted to the bench and including motorized toothed members adapted to couple with the toothed guides of the containers for horizontally moving the latter between the access area of the storage and the bench, and a control unit adapted to coordinate the devices during the loading/unloading operations.

5 Claims, 14 Drawing Sheets

APPARATUS FOR AUTOMATICALLY DEPOSITING, PRESERVING AND RETRIEVING BIOLOGICAL MATERIAL SPECIMENS IN A REFRIGERATED STORAGE

The present invention concerns an apparatus for automatically depositing, preserving and retrieving biological material specimens in a refrigerated storage.

The term "laboratory medicine" means the set of diagnostic services which operate on biological materials collected from patients.

In addition to the true tests performed on biological materials, such diagnostic services also include the gathering and interpreting of analytic data from different specialized departments with the purpose of being able to clearly and accurately diagnose the patient.

In general, the values obtained from chemical tests performed on biological material specimens are compared with the ranges of values deemed physiological; following the medical history, a physical examination and other possible specialized examinations, doctors may then be able to formulate a pathological diagnosis. However, following the results of a test on a given biological material specimen, a second series of tests may often need to be carried out on the same specimen in order to check, and possibly validate, the obtained results. Such a need may be satisfied only by ensuring an adequate preservation of the specimen over time, so that such a specimen may be subjected to other tests even a few days after collection, without any decay which would make impossible to perform further tests on the same.

For this reason, many test laboratories are now provided with refrigerated storages, adapted to preserve biological material specimens at controlled temperatures, ensuring the integrity thereof and the possibility of using such specimens also after several days from the collection time.

The step of placing the specimens, once the related containers have been appropriately closed inside the storages, is a process which, as the previous steps of specimen processing and testing, requires a high level of manual dexterity by the laboratory operators who are responsible for managing biological material specimens.

Such a human intervention in handling the specimens has several disadvantages, such as for example the introduction of human errors in the preparing, testing and preserving process of the specimens themselves, the slowdown of the test procedures and risks for the operators who could come into contact with potentially infected biological fluids.

For these reasons, the introduction of technologies aimed at obtaining a high level of automation of the working cycle performed on specimens may be currently observed, above all in those large-sized laboratories which undergo high work loads daily.

Such an automation has the main object of making the results of the tests performed on specimens safer and more reliable, thus eliminating the probability of human errors to the greatest possible extent, in addition to making the processing of said specimens faster and safer for laboratory operators. The common desire today is to limit the contact of operators with biological material as much as possible, in order to ensure safety to the operator at work and limit the presence of human errors in the processing of biological material specimens.

The introduction of laboratory automation, in addition to involving the steps of pre-testing the specimens (such as, in the case of blood, container opening, centrifugation, aliquoting) and testing (collection of the specimens contained in the specific containers by means of needles and chemical tests thereon), also concerned the subsequent steps of post-testing (e.g. sealing the containers containing the residual specimen at the end of the tests and placing the same in refrigerated storages), having the purpose of ensuring an appropriate preservation of the biological material specimens, thus allowing a possible subsequent step of testing.

Furthermore, in order to make the whole process on a specimen homogenous and reliable, the aim is to automate such a working cycle as a whole, by introducing mechanical arms and conveyor belts adapted to handle and transport the specimens on belts connected to devices adapted to perform various types of processing required to obtain the results on the specimens (steps of pre-testing, testing and post-testing). US 2007/172396 and U.S. Pat No. 7,214,023 disclose apparatuses for loading and unloading refrigerated storage of containers of test tubes.

It is the object of the present invention to make an apparatus adapted to automate the depositing process and the possible retrieving of biological material specimens in an integrated refrigerated storage, possibly in an apparatus adapted to transport the biological material specimens, connected in turn to further preparing and testing devices.

In accordance with the invention, the object is achieved by an apparatus as disclosed in claim 1.

It is assumed that the test tube which is presented at the loading/unloading point on the conveyor is sealed (either with its original cap or appropriate, previously applied sealing material) and previously identified, by reading the bar code placed on said test tube, by a bar code reader or other possible identification devices.

Generally, two main operations may be carried out in the described apparatus:

loading the test tube from the loading/unloading point on the conveyor belt inside the refrigerated storage;

unloading the test tube from the refrigerated storage at the loading/unloading point on the conveyor belt or into the unloading tube.

During the step of loading, an empty test tube container is withdrawn from the refrigerated storage to the bench. A test tube, which is presented at the loading/unloading point on the conveyor belt, is placed by the test tube handling device in an available location of the test tube container on the bench. When all locations of the test tube container are loaded with test tubes, the container handling device inserts the test tube container into the storage, thus placing it in the same lane of the same shelf which it previously occupied. The control unit associates the identification code of the test tube with the identification code of the test tube container, with its position in the storage and with the location in which the test tube was placed in the container. In such a manner, the position of the test tube inside the storage is univocally known.

During the step of returning the test tube, the test tube container containing the desired test tube (the position of which inside the storage is known because it has been stored during the step of loading) is moved from the interior of the storage onto the bench, and the test tube handling device moves the required test tube from the location in the test tube container (stored during the step of loading) by placing it at the loading/unloading point on the conveyor belt or, if the biological material contained in the test tube is no longer intact, into the unloading tube. When a test tube is unloaded from the refrigerated storage at the loading/unloading point on the conveyor belt, it may then be conveyed to the processing and testing modules, according to the operations which must be performed on said test tube.

These and other features of the present invention will be more apparent from the following detailed description of a practical embodiment thereof shown by way of non-limitative example in the accompanying drawings, in which.

Figure 1:
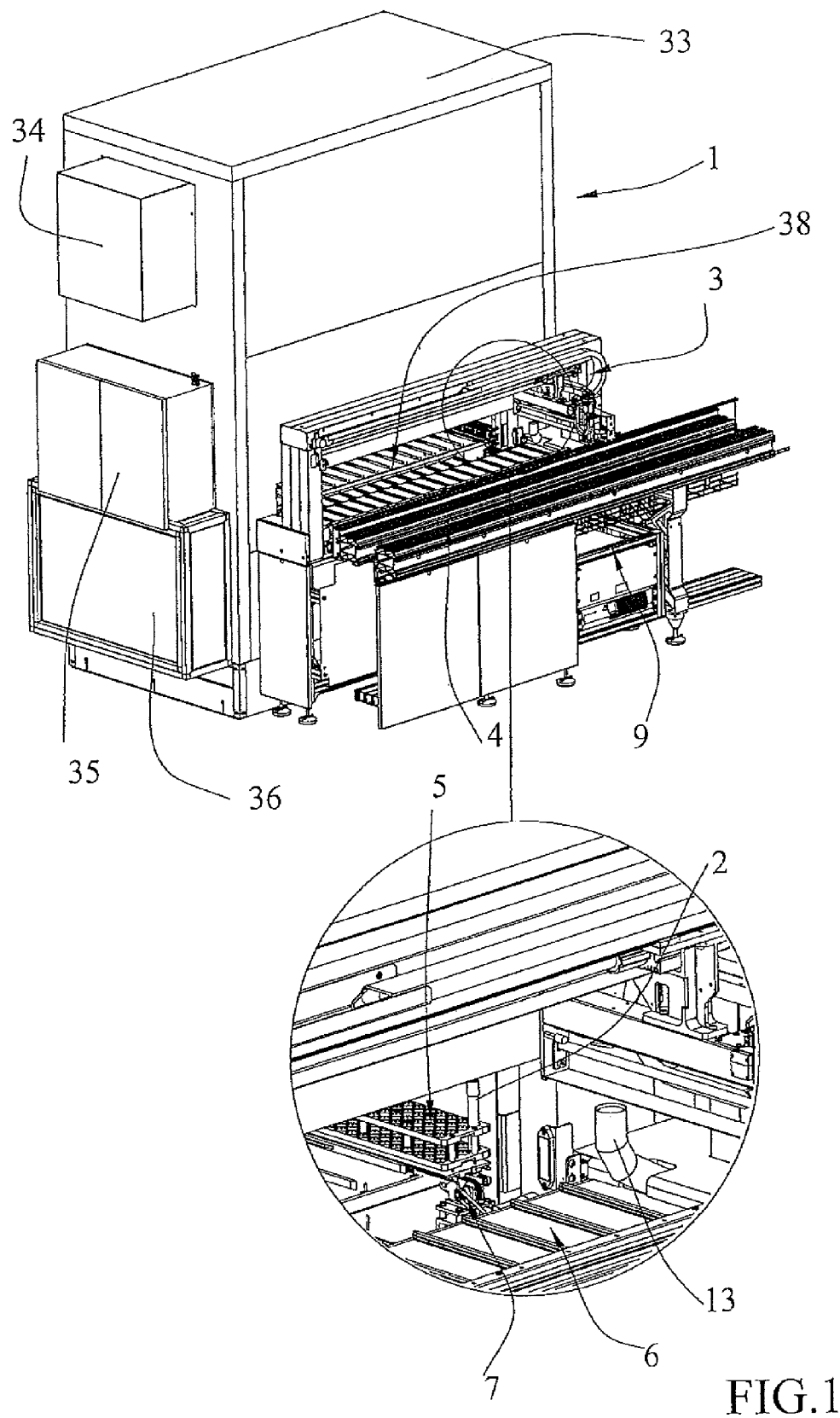
FIG. 1 shows a perspective view of the apparatus according to the present invention.
Figure 15:
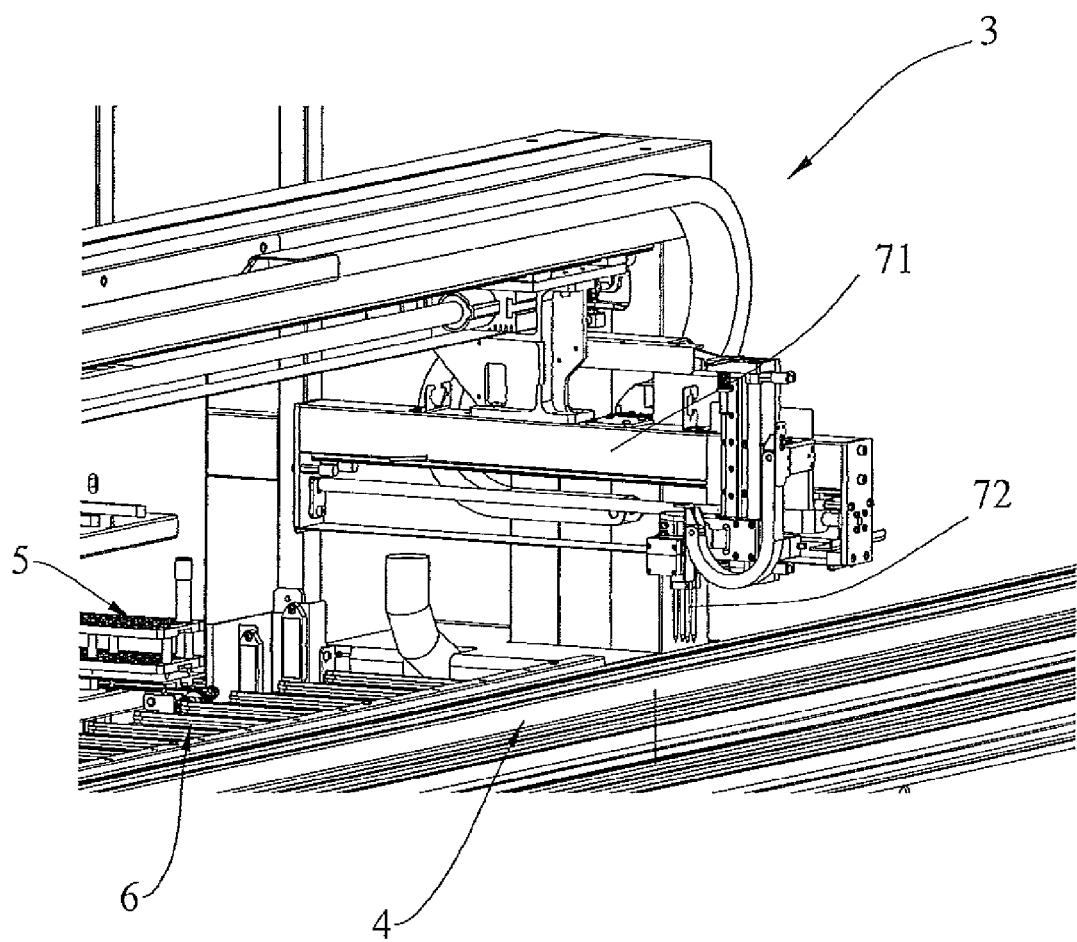
FIG. 15 shows a perspective view of the handling device adapted to handle test tubes.

FIG. 1 shows an apparatus for automatically depositing, preserving and retrieving biological material specimens in a refrigerated storage 1, adapted to accommodate and preserve biological material containers, e.g. test tubes 2, which are handled one by one by means of a test tube handling device 3 (FIG. 15) between an interface 4 of a test tube conveyor and appropriate containers 5 of a sorted plurality of test tubes (multiple test tube containers or racks 5).

Said test tube containers 5 are placed on a bench 6 outside the storage 1 during the step of loading/unloading the test tubes 2 and inserted into the refrigerated storage 1 by means of an appropriate container handling device 7 at the end of said loading/unloading operation.

In the described embodiment, the interface 4 is included in an external apparatus for automatically handling test tubes (FIG. 1), e.g. a conveyor belt, adapted to transport the biological material test tubes to preparing and testing modules interfaced with said conveyor belt.

The test tube handling device 3 consists of a mechanical arm 71 comprising a gripper 72 (FIG. 15) adapted to grip the test tubes 2 during the step of handling the same. Said mechanical arm 71 is able to perform translating movements in the three dimensions, reaching all the points required for carrying out the correct test tube handling process, according to the commands sent by a control unit 9.

The control unit 9 (FIG. 1) is an application software installed on a personal computer, provided with a memory containing all the information needed to perform the correct activities on the test tubes and adapted to store the lifecycle during the process; furthermore, it serves the function of coordinating the devices involved in the test tube loading/unloading operations.

Figure 3:
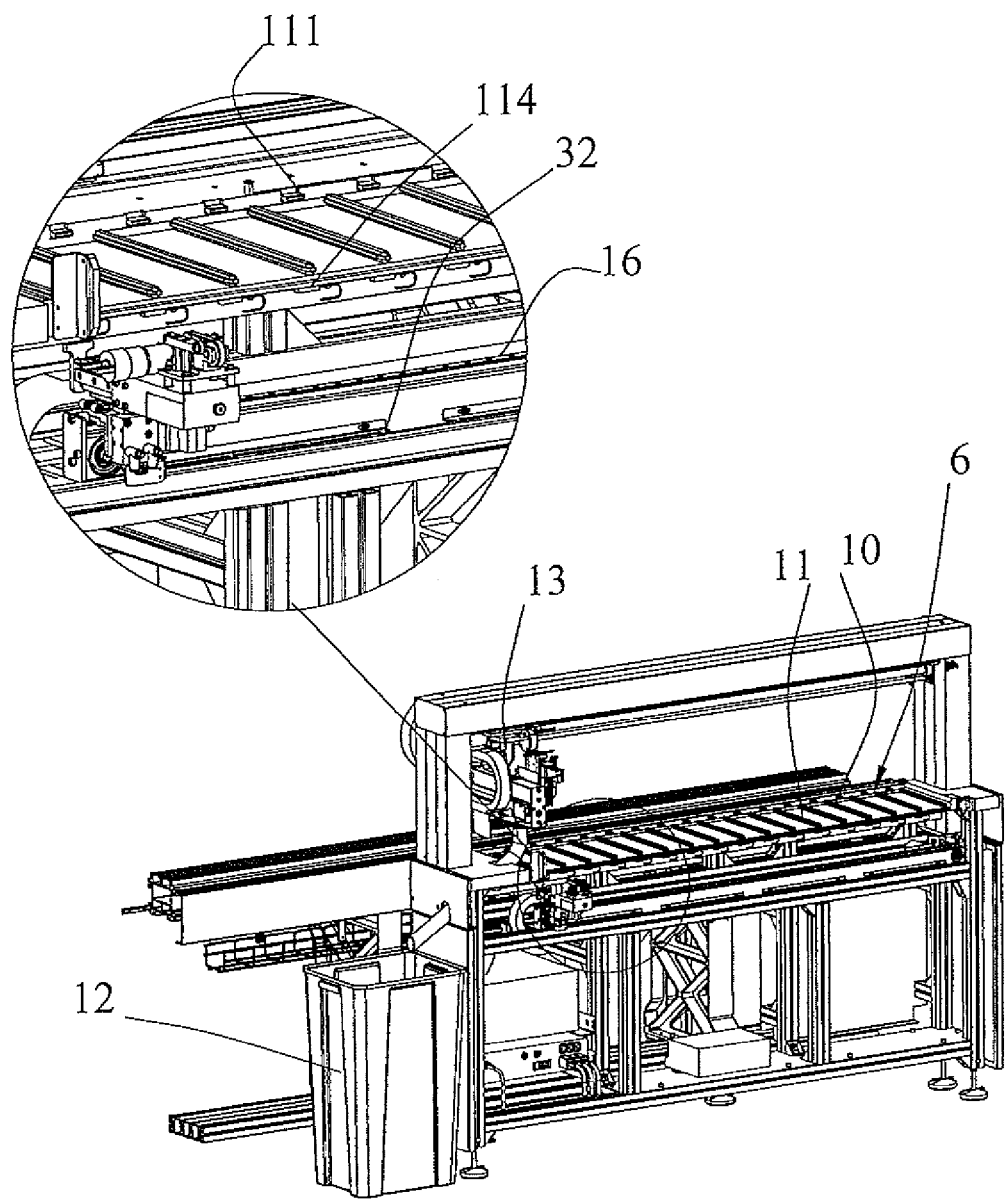
FIG. 3 shows a perspective view of the loading/unloading bench on the storage side, the storage being removed.
Figure 14:
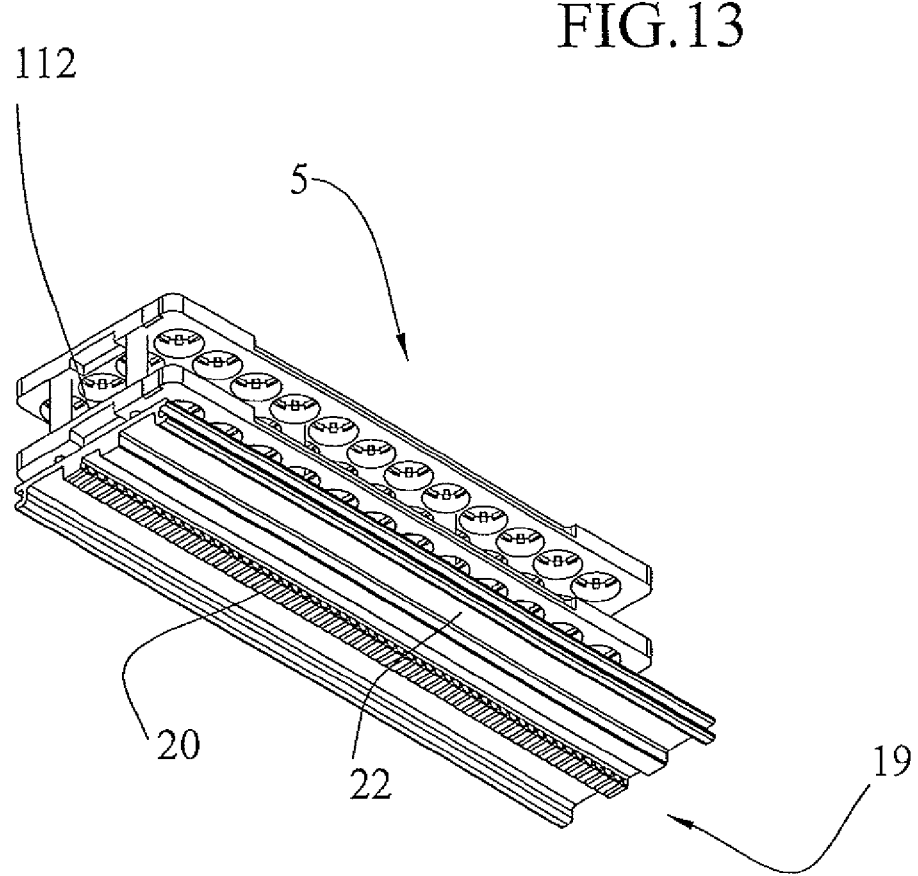
FIG. 14 shows a perspective view of the lower surface of the test tube container.

The bench 6 shown in FIG. 3 consists of guides 10 which in twos form the lanes 11 adapted to accommodate the test tube containers 5. When a test tube container 5 is inserted into a lane 11, a coupler 111 (FIG. 3) at the end of said lane, by being inserted into the housing 112 (FIG. 14) of the test tube container 5, ensures the stability thereof during the test tube loading/unloading operations by the test tube handling device 3. In the described embodiment, there are sixteen lanes, but such a number may vary according to the desired size of the described apparatus.

The test tubes 2 preserved in the test tube containers 5 inside the refrigerated storage 1 have a maximum stay time after which they are eliminated because the biological material contained therein is no longer considered intact and thus is not usable for diagnostic purposes. Such a time is a parameter which may be configured in the control unit 9.

A test tube container 5 containing the test tubes 2 which have exceeded the maximum stay time inside the refrigerated storage 1 is moved from the refrigerated storage to the bench 6 where the test tube handling device 3 has the task of removing the test tube contained in said test tube container 5 one by one, rejecting them into a specific test tube unloading collector 12 (FIG. 3) by means of a tube 13. At the end of said unloading operation, the emptied test tube container 5 is introduced back into the refrigerated storage 1.

The handling activity of test tube containers 5 from the interior to the exterior of the refrigerated storage 1 and vice versa is allowed by the presence of a container handling device 7 (FIGS. 1 and 6), capable of running parallel to the bench 6 by means of a carriage 15 along a sliding guide 16 (FIG. 3) mounted to the lower part of said bench. A belt actuated by an electric motor slides on said sliding guide 16; such a sliding allows the container handling device 7 to reach all the lanes 11 on the bench 6.

Figure 5:
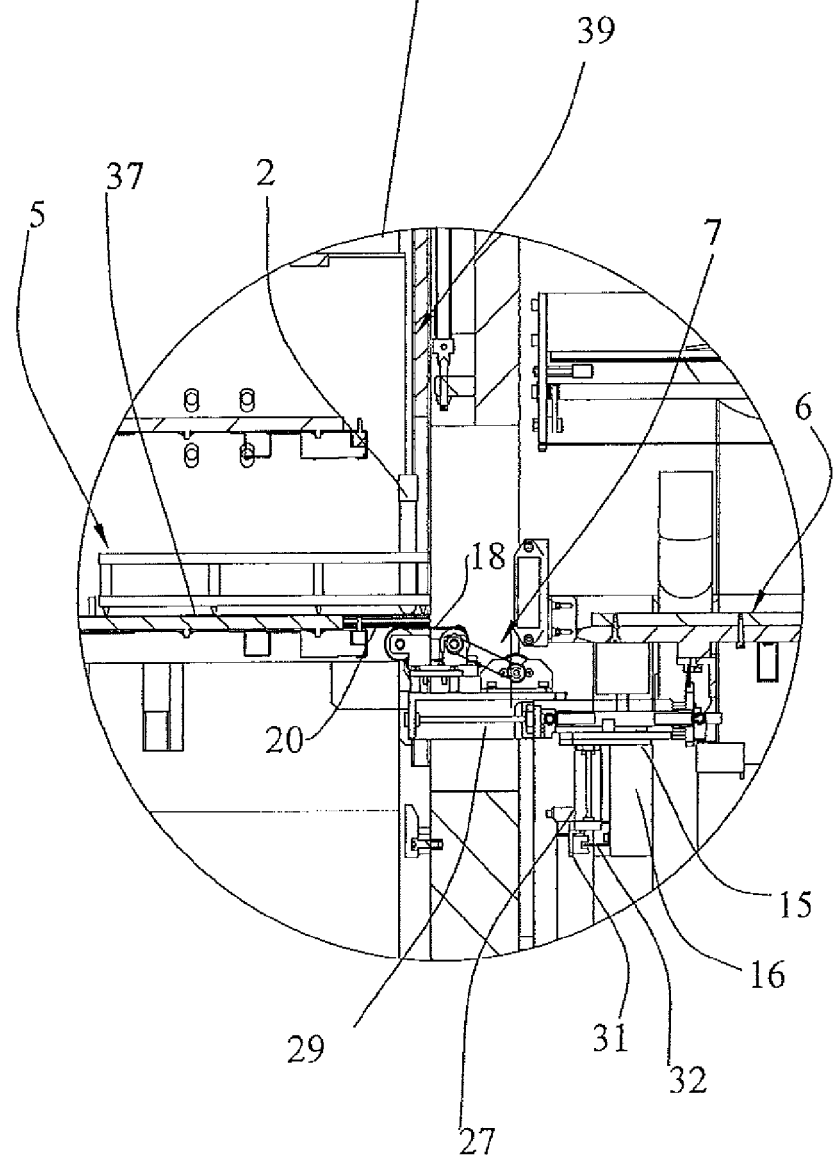
FIG. 5 shows the configuration in FIG. 4 with the container handling device in loading position and the sliding door open.

To a support 17 (FIG. 6) of said device 7, a toothed translation track 18 is mounted, which allows the test tube container 5 to slide thus translating from the bench 6 to the refrigerated storage 1 and vice versa, as shown in FIG. 5.

Figure 13:
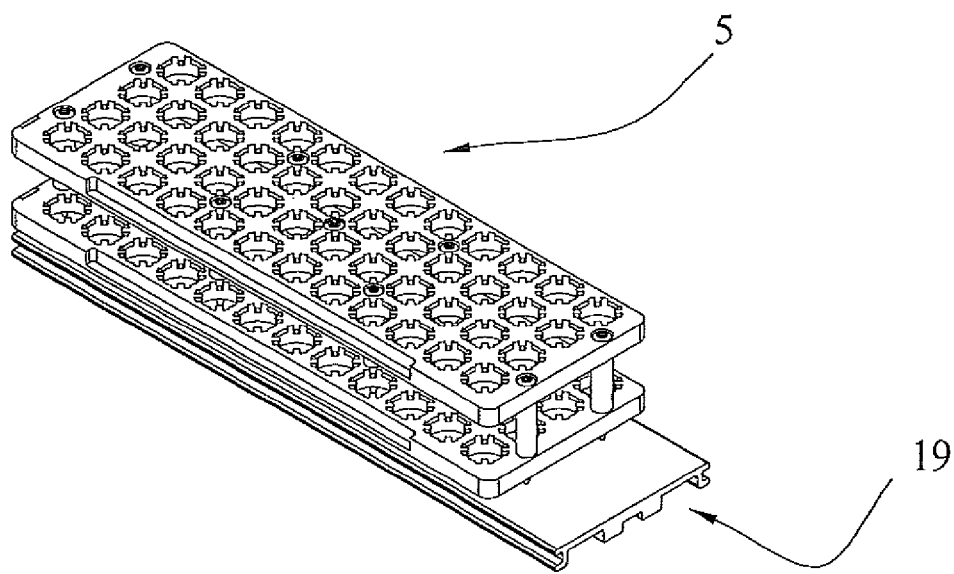
FIG. 13 shows a perspective view of the test tube container.

The lower surface 19 (FIGS. 13 and 14) of the test tube container 5 is provided with a toothed guide 20 such as to allow the translation of said test tube container 5 on the toothed translation track 18.

Sliding bearings 21 (FIG. 6) ensure the balancing of the test tube container 5 along a guide 22 of the container 5 (FIG. 14) during the translation.

Figure 6:
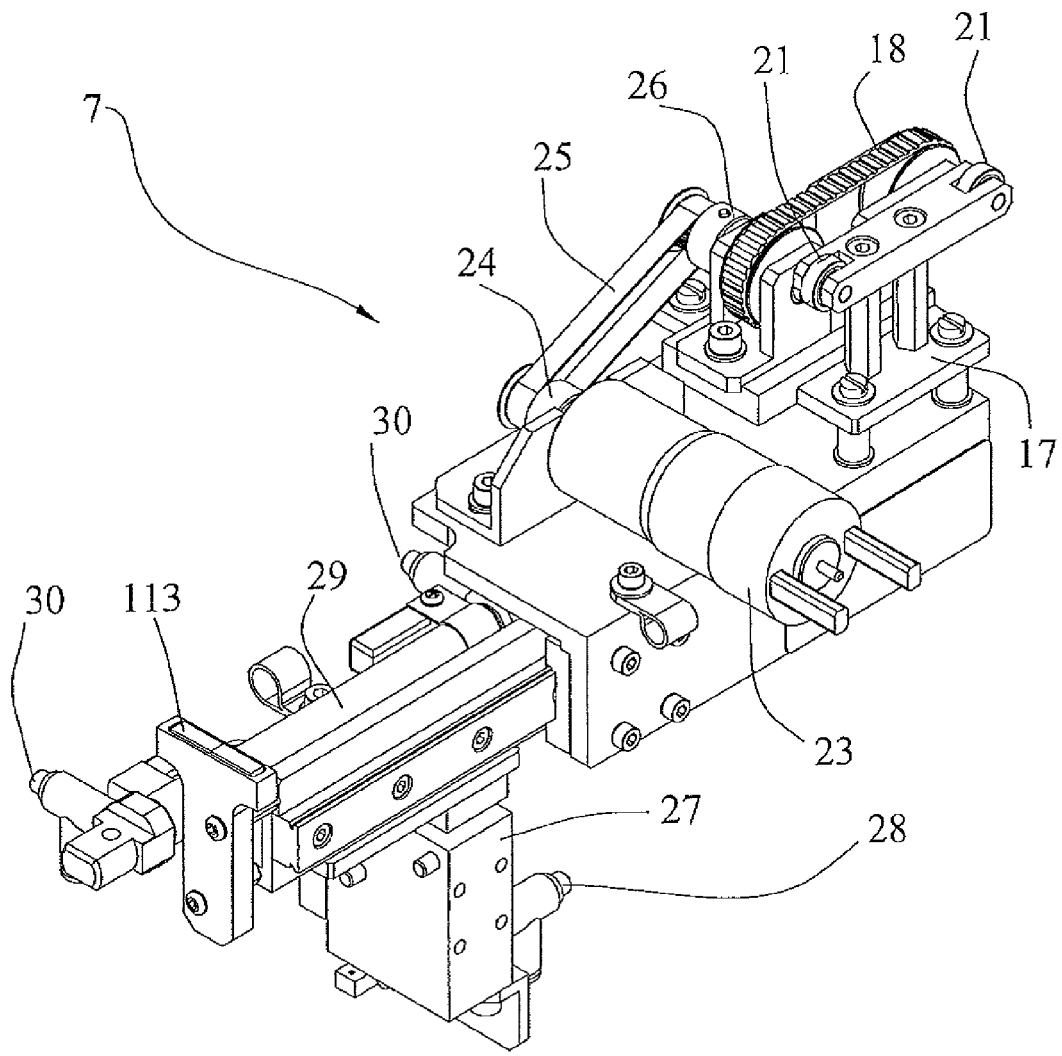
FIG. 6 shows a perspective view of the container handling device.

The movement of the toothed translation track 18 is generated by an electric motor 23, the movement of which is transmitted from a shaft 24 to a pulley 26 by means of a belt 25 (FIG. 6).

Figure 4:
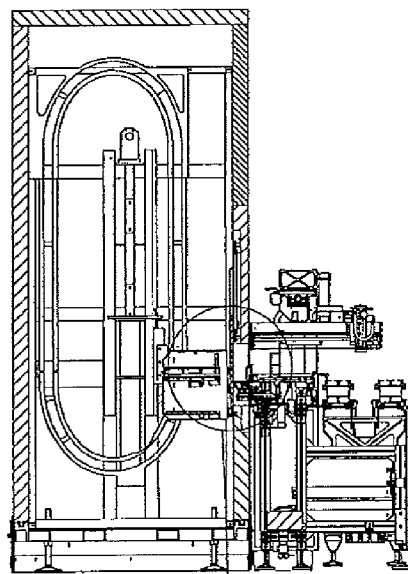
FIG. 4 shows a side section according to line IV-IV in FIG. 2 in which the container handling device is in a rest position and the sliding door is closed.
Figure 4:
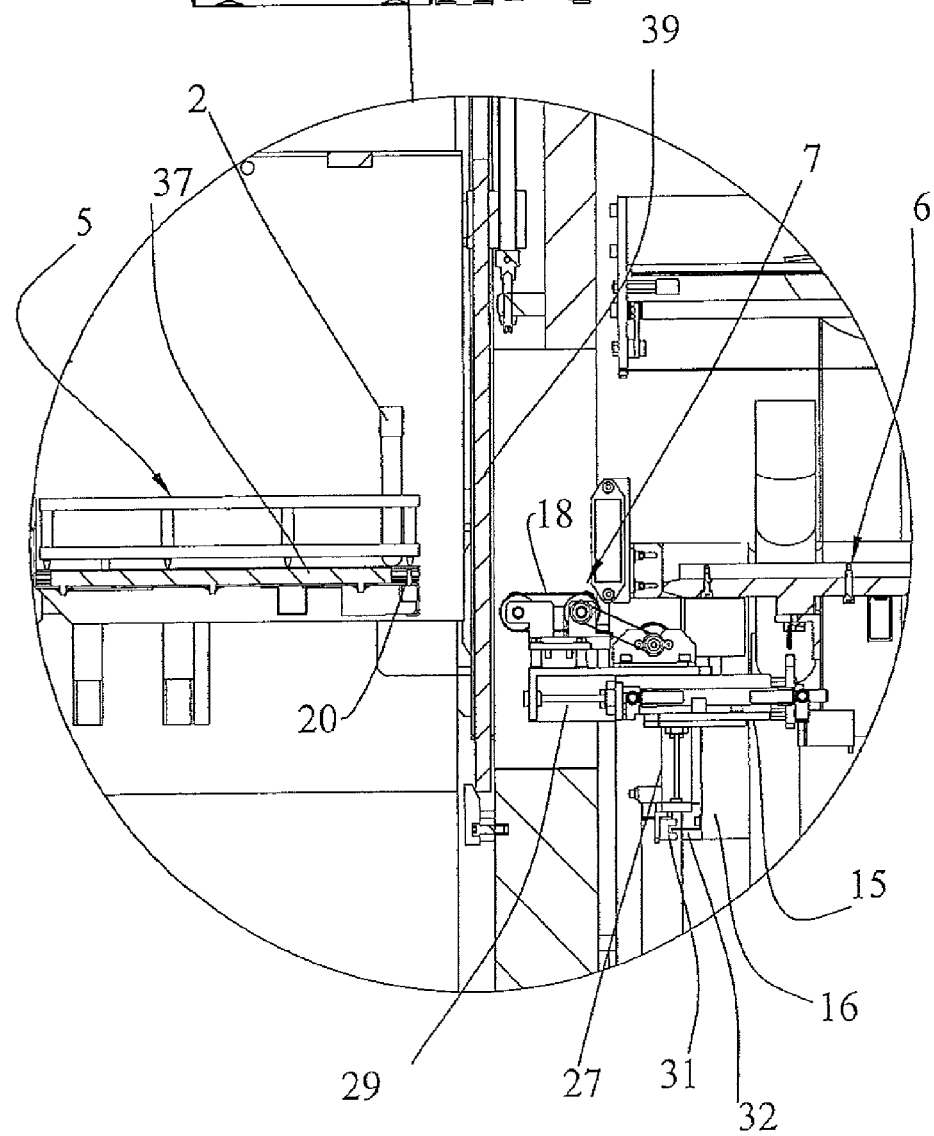
Figure 7:
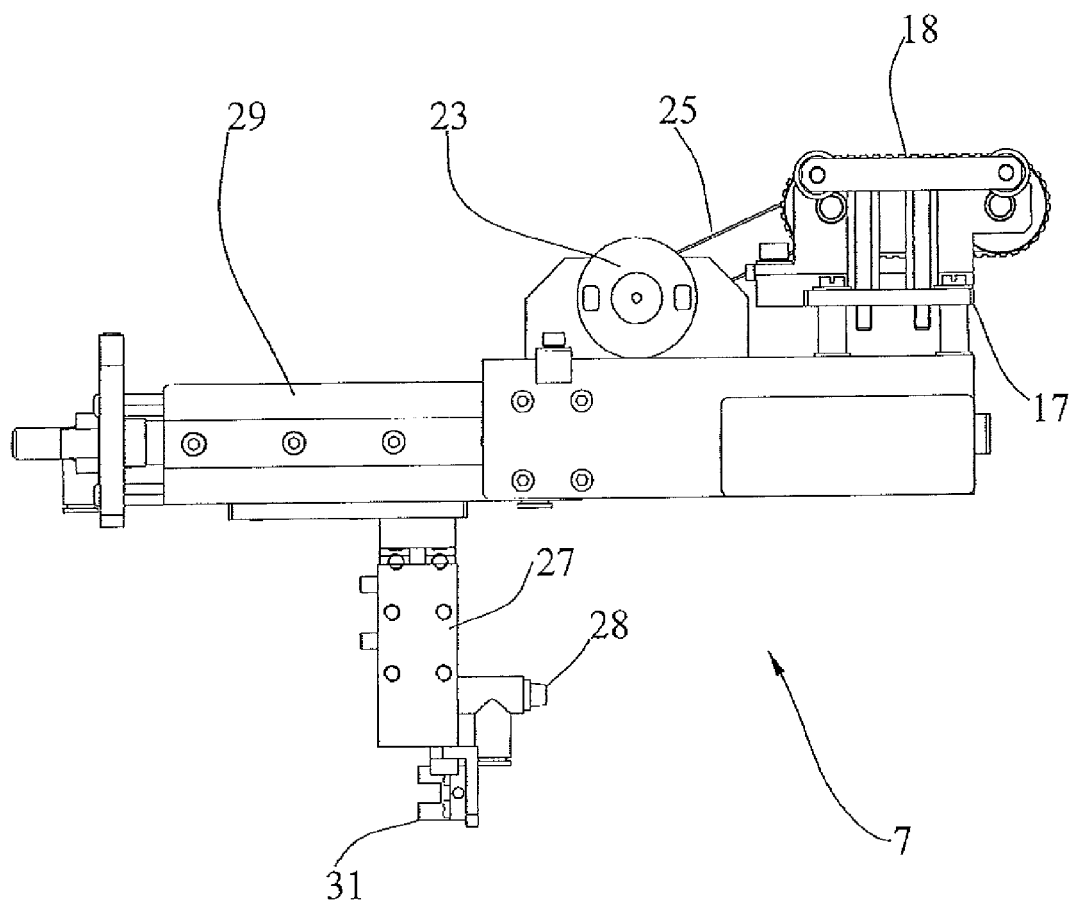
FIG. 7 shows a right side view of the container handling device.

In the rest position, the container handling device 7 is in the "low" position, as shown in FIG. 4, while when handling the test tube containers 5 from the refrigerated storage 1 to the bench 6, or vice versa, said container handling device 7 is arranged in the "high" position, as shown in FIG. 5. Such a vertical translation is ensured by a pneumatic cylinder 27, fed by solenoid valves by means of two flow adjusters 28 (FIGS. 6-8).

Figure 8:
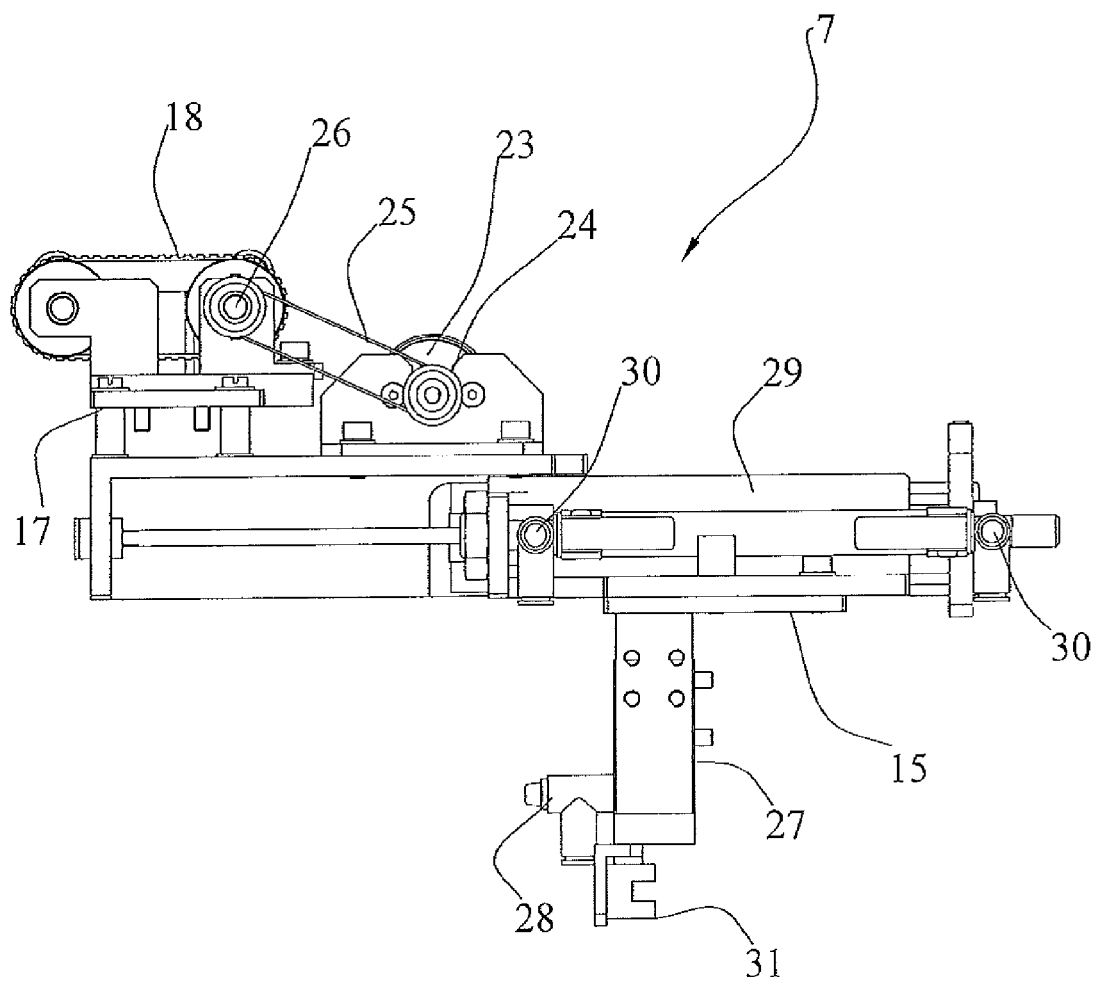
FIG. 8 shows a left side view of the container handling device.

The movement in a perpendicular direction to the bench 6, allowing the movement from the rest position close to the bench 6, in the direction of the refrigerated storage 1, and vice versa, is ensured by a pneumatic cylinder 29 fed by solenoid valves by means of two flow adjusters 30 (FIGS. 6 and 8).

Figure 9:
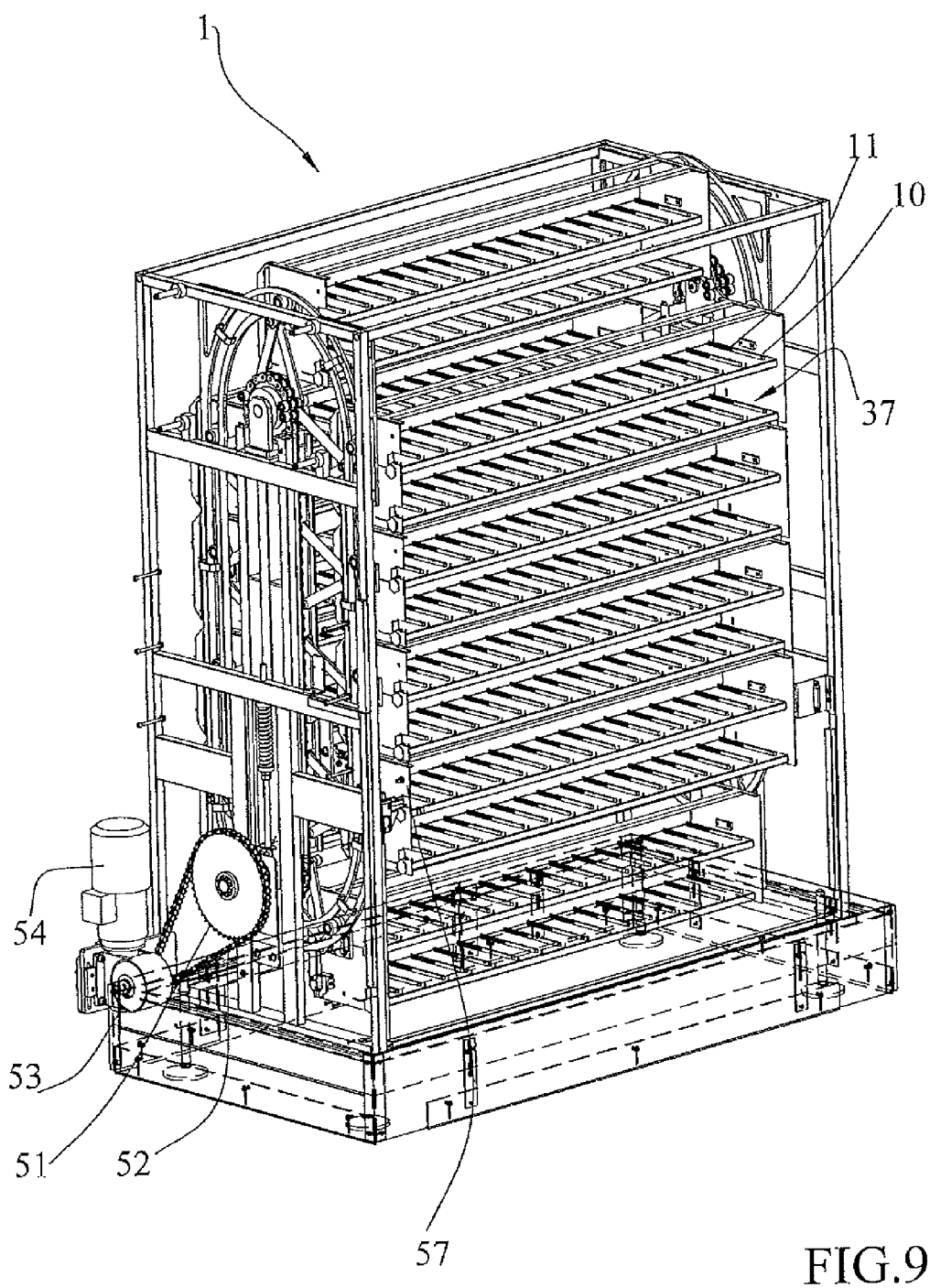
FIG. 9 shows a perspective view of the storage without external guards.

The refrigerated storage 1 is a cold store enclosed by external panels 33 adapted to ensure the insulation thereof from the outside (FIG. 1). Said cold store is provided with a temperature sensor, which by monitoring the temperature inside the cell, manages the operation of the refrigerator 34, placed on the side wall of the refrigerated storage 1, so as to keep the required temperature constant. In addition to the refrigerator 34, the electric panel 35 and the motors 36 adapted to mechanically handle the shelves 37 and protected by panels, are present on the side wall of the refrigerated storage (FIGS. 1 and 9).

Figure 2:
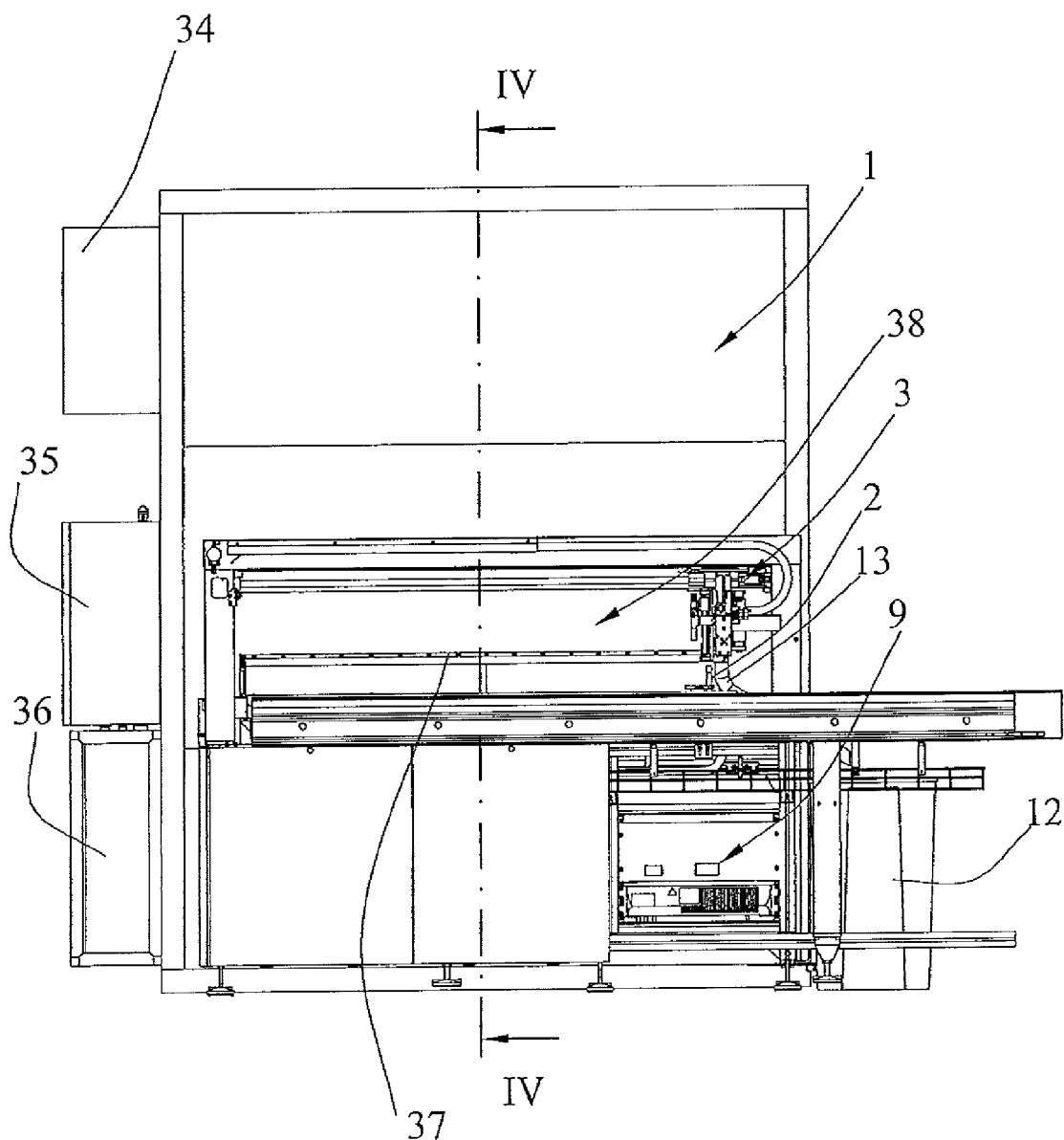
FIG. 2 shows a front view of the configuration in FIG. 1.

The presence of an access area 38 (FIGS. 1 and 2) allows the refrigerated storage 1 to communicate with the bench 6. In the described embodiment, said access area 38 is protected by a sliding door 39 (FIGS. 4 and 5) adapted to ensure the thermal insulation of the refrigerated storage 1. Such a sliding door 39 opens, by means of a command sent by the control unit 9, whenever a test tube container 5 needs to be handled from the refrigerated storage 1 to the bench 6, or vice versa.

Alternatively, a door, functionally equivalent to the sliding door 39, may be present close to each lane, so as to ensure only the opening of the area corresponding to the lane involved in the test tube container handling operation.

Figure 12:
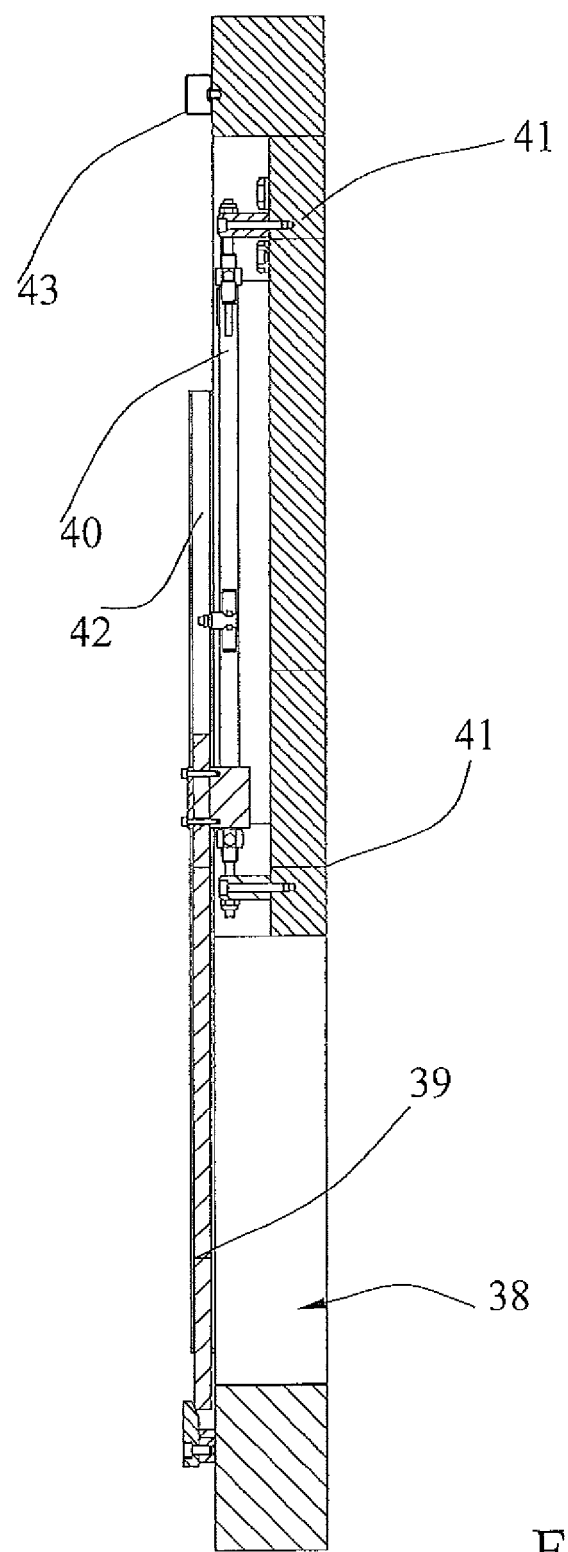
FIG. 12 shows a section of the deposit panel on which the sliding door is installed.

FIG. 12 shows a first shelf of the section of the refrigerated storage 1 at the sliding door 39. A pneumatic cylinder 40, fed by solenoid valves by means of flow adjusters 41, ensures the sliding of the sliding door 39 in the guide 42. The sliding door 39 have two configurations: a closed configuration (FIGS. 4 and 12) and an open configuration (FIG. 5). An electromagnetic sensor 43 (FIG. 12), being activated when the door is in the open configuration, monitors the actual "open" state thereof. Such an electromagnetic sensor 43 allows the control unit 9 to monitor possible faults in the closing/opening operation of the sliding door 39.

FIG. 9 shows the refrigerated storage 1 with the external panels 33 being removed. Shelves 37 are present for accommodating the test tube containers 5 in the refrigerated storage 1. Said shelves 37 accommodate guides 10 adapted to form lanes 11 equivalent to the lanes 11 on the bench 6 and the number of lanes present on a shelf 37 is equal to the number of lanes present on the bench (sixteen, in this embodiment).

Figure 10:
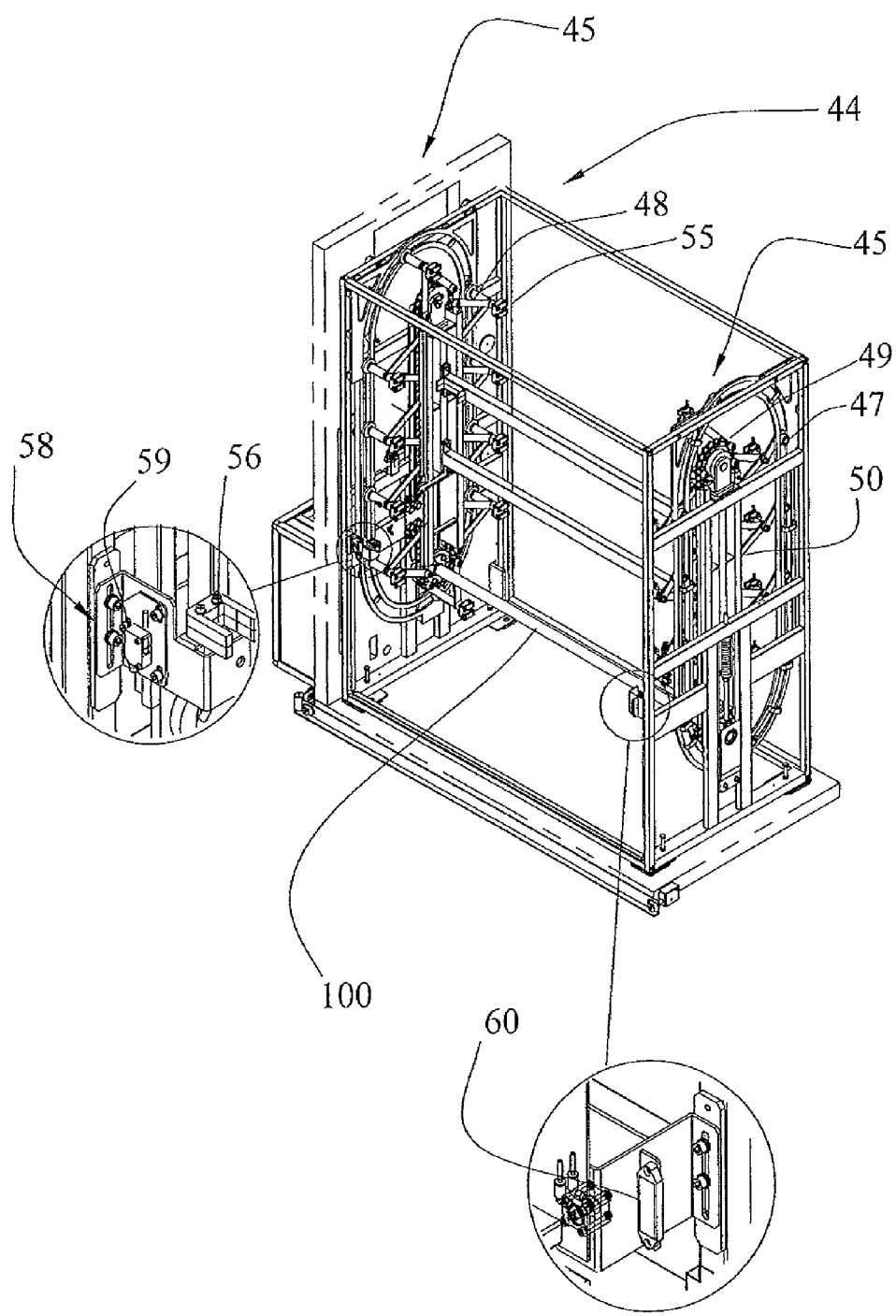
FIG. 10 shows a perspective view of the storage without external guards and without shelves, in which the shelf rotating device is highlighted.
Figure 11:
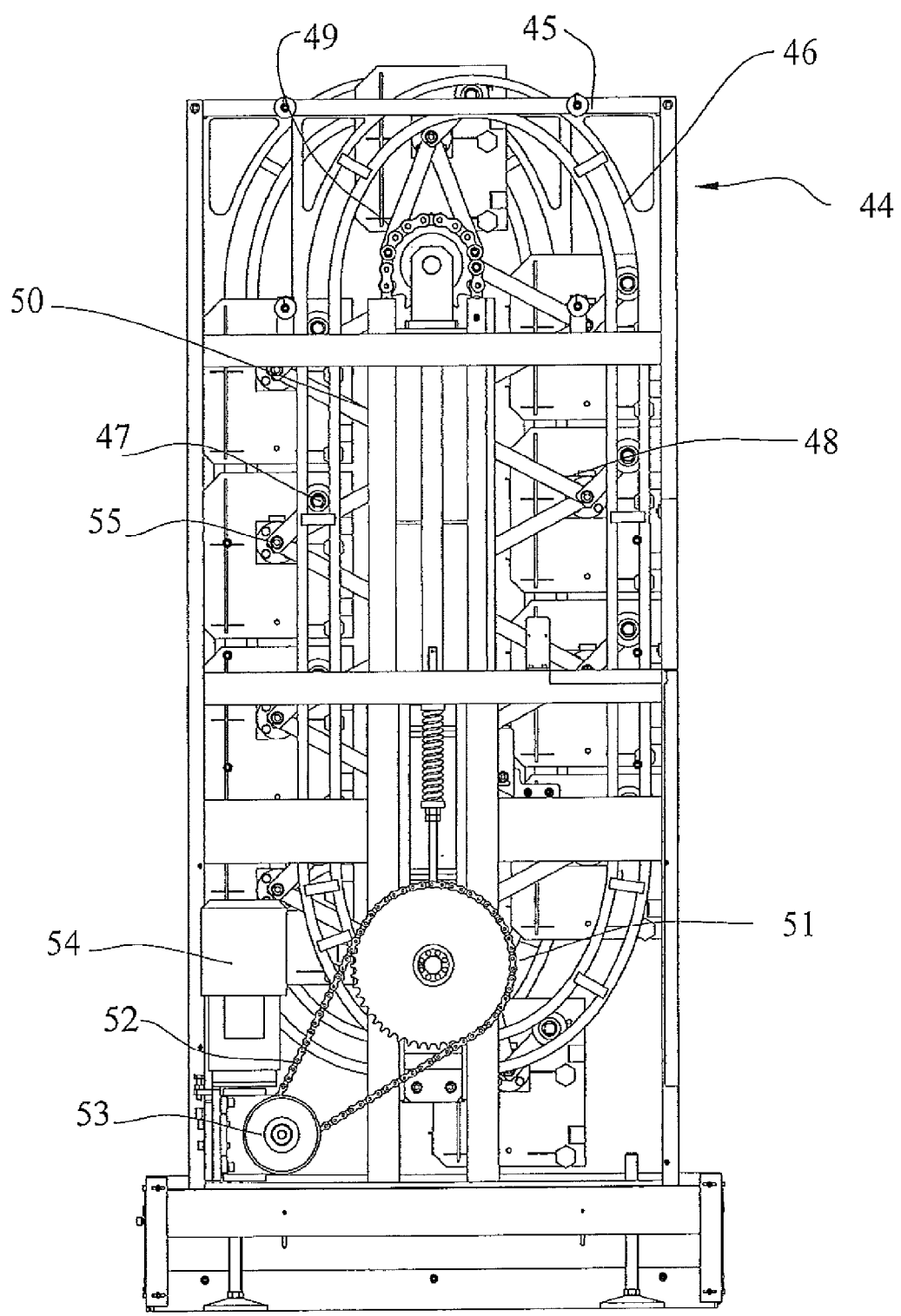
FIG. 11 shows a side view of the wall of the storage in which the motor drive of the shelf handling device is placed.

The storage 1 includes a shelf handling mechanism 44 comprising two structures 45 placed on the side walls of the refrigerated storage 1 (FIGS. 10 and 11). Such structures 45 consist of guides 46 in which rollers 47 hinged to lever mechanisms 48 slide (FIG. 11). Said lever mechanisms 48 are, in turn, hinged to a chain 49, which slides in a guide 50 placed inside the guide 46. The chain 49 is rotated by a toothed wheel 51, rotated in turn by a chain 52, moved by a motor reducer 53 actuated by a motor 54 (FIGS. 9 and 11)

Following a handling command of a test tube container 5 from the refrigerated storage 1 to the bench 6, or vice versa, sent by the control unit 9, the container handling device 7, by sliding on the sliding guide 16, is placed close to the lane 11 involved in the operation. The sureness that the correct lane has been reached is given by the presence of a photoelectric reference sensor 31 (FIG. 7), which when the container handling device 7 slides along the sliding lane 16, engages reference notches 32 present at each lane 11 (FIGS. 3, 4 and 5).

A counter allows to store the number of the "reached" notch with respect to a reference point (e.g. the rest position corresponding to the first lane 11 of the bench 6, as shown in FIG. 1) and allows the container handling device 7 to stop close to the required lane 11.

Once the correct lane 11 is reached, the container handling device 7 is taken from the "low" position to the "high" position (as shown in FIGS. 4 and 5, respectively). Following the upward placing of the container handling device 7, a proximity switch 113 (FIG. 6), consisting of a magnet, comes in contact with a magnet 114 (FIG. 3), placed in the lower part of the bench 6 at each lane, causing the actuation of a circuit which determines a rising of the coupler 111.

Such a rising allows to handle the test tube containers, specifically allows them to be moved from the bench 6 to the refrigerated storage 1 or, in the case of the reverse operation, to be inserted into the lane 11 on the bench.

When at the end of the operation the container handling device 7 returns to the "low" position, the deactivation of the circuit determines the lowering of the coupler 111 and, if a test tube container 5 is inserted into a lane 11 on the bench 6, the consequent blocking of said container 5.

According to the operation to be performed, the movement in a direction perpendicular to the bench 6 carried out by the pneumatic cylinder 29 occurs: if the test tube container 5 must be moved from the refrigerated storage 1 to the bench 6, the container handling device 7 is arranged in the configuration in FIG. 5 and during the translation of the test tube container 5 on the toothed translation track 18, it moves downwards; and vice versa, if the test tube container 5 must be moved from the bench 6 to the refrigerated storage 1.

Only one test tube container 5 corresponds to each lane 11 of each shelf identified by the control unit 9 by means of the corresponding location inside the refrigerated storage 1. Said location corresponds to the shelf number and corresponding lane in which the test tube container is placed. When a test tube container 5 is moved on the bench 6 for a loading or unloading operation of test tube 2, at the end of the operation such a test tube container 5 is placed again inside the refrigerated storage 1 in the same position (shelf and corresponding lane) in which it was found.

During a handling operation of test tube containers 5, the shelf handling mechanism 44 (FIG. 10) allows the shelf containing the requested test tube container 5 to place itself close to the access area 38, at a height (as shown in FIG. 5) so that the translation of the test tube container 5 from the bench 6 to the refrigerated storage 1, or vice versa, is perfectly horizontal. The movement of the chain 49 along the guide 50 moves the lever mechanisms 48, to which the shelves 37 are coupled by means of the supports 55 (FIGS. 10 and 11).

The motion of the motor 54 is transferred to the structure 45 placed on the opposite side wall by means of a shaft 100 (FIG. 10).

Such a shelf handling mechanism 44 ensures the horizontality of the shelves 37 during their rotary movement. The horizontal position of the moving shelves 37 is a necessary requirement for ensuring that the test tubes 2 in the test tube container 5 are not subjected to upturning or slanting during the shelf handling operations.

A position sensor 56, placed on the left side wall inside the refrigerated storage (FIG. 10) serves the function of shelf counter. Said position sensor 56 consists of two optical fibers, which detect the passage of a tab 57 placed on the external side wall of the shelves (FIG. 9) during the movement thereof. The position sensor 56 allows the control unit 9 to know the position of the shelves inside the refrigerated storage 1.

A further check is carried out by means of a barrier 58 (FIG. 10) serving the function of detecting whether a test tube container 5 is present or not when handling the same from the refrigerated storage 1 to the bench 6, and vice versa. Said barrier 58 consists of a laser beam emitter 59 towards a receiver 60. During the passage of a test tube container 5, the interruption of the laser beam is detected by the receiver 60, thus allowing the control unit to monitor the handling of a test tube container 5, also determining the closing of the sliding door 39 at the end of the handling operation.

A bench 6 may accommodate several containers 5 at the same time, having other purposes according to the action which is being performed thereon, as will be described below.

The presence of a multi-lane bench, capable of accommodating several test tube containers at the same time, allows the apparatus for automatically depositing and retrieving biological material specimens to simultaneously perform different operations on the test tubes.

In this case, an empty test tube container during the step of loading, a test tube container during the step of unloading test tubes for which the maximum integrity time has expired and a test tube container withdrawn onto the bench because it contains a test tube to be unloaded at the loading/unloading point for further processing may be present at the same time on the bench. The control unit is capable of coordinating the actions of the devices involved in such operations.

The capacity of the described apparatus to carry out different operations at the same time ensures to speed up the loading/unloading process allowing such an apparatus to be also used by laboratories subjected to major work flows.

The invention claimed is:

1. An apparatus for automatically depositing, preserving and retrieving biological material test tubes, comprising:
   - at least one rack configured to hold a plurality of test tubes, said rack including toothed guides on the bottom surface;
   - a refrigerated storage with movable horizontal shelves;
   - a conveyor interface configured to automatically transport single biological material test tubes;
   - a test tube handling device configured to handle a single test tube between the interface and the at least one rack, each rack being able to be placed on one of a plurality of lanes of a bench facing the conveyor interface, each horizontal shelf of said refrigerated storage having a number of lanes housing at least one rack corresponding to the number of lanes of the bench, each lane of the shelf being faced to a respective lane of the bench when the shelf is aligned with the bench;
   - a rack handling device including a motorized toothed translation track engaging said toothed guides of the at least one rack for moving the at least one rack between a lane of the bench and a corresponding faced lane of a shelf of the refrigerated storage aligned with the bench, said rack handling device being able to run parallel to the bench in order to reach every lane of the bench, said rack handling device comprises a proximity switch configured to be coupled with magnets of each lane of the bench to activate a circuit for releasing the corresponding racks in the lanes of the bench, said proximity switch also configured to activate a vertical and horizontal translation means of the motorized toothed translation track to begin transport of the rack by the rack handling device, and a reference photoelectric sensor configured to engage reference notches at each lane; and
   - a control unit configured to coordinate said test tube handling device and said rack handling device during the loading/unloading operations by means of locating means configured to locate each test tube in the refrigerated storage, by identifying the rack which contains it, the position of the test tube in the rack, the shelf and the lane of said shelf containing the rack, thus allowing the automatic retrieval of said test tube from the refrigerated storage from any point therein and at any time.

2. The apparatus according to claim 1, wherein said control unit configured to monitor the stay time of the test tubes in the refrigerated storage with respect to a reference period, rejecting the expired test tubes by means of the test tube handling device is configured to handle the test tubes between the at least one rack and an expired test tube collector.

3. The apparatus according to claim 1, wherein said refrigerated storage comprises two carrying structures having guides on which rollers hinged to lever mechanisms slide, which structures support said movable horizontal shelves and are hinged, in turn, to a chain actuated by a motorized toothed wheel.

4. The apparatus according to claim 1, wherein said refrigerated storage comprises a shelf counter including a pair of optical fibers which detect the passage of a tab placed on the external wall of the shelves, and an emitter-receiver pair configured to detect the presence of a rack during the handling between the refrigerated storage and the bench.

5. The apparatus according to claim 1, wherein said refrigerated storage comprises a sliding door controlled by the control unit.

* * * * *